United States Patent [19]
Maycock et al.

[11] Patent Number: 5,811,078
[45] Date of Patent: *Sep. 22, 1998

[54] SPRAY FORMULATIONS OF ANTIHYPERALGESIC OPIATES AND METHOD OF TREATING TOPICAL HYPERALGESIC CONDITIONS THEREWITH

[75] Inventors: Alan L. Maycock, Malvern; An-Chih Chang, Phoenixville; John J. Farrar, Chester Springs; Imre Balogh, Perkasie, all of Pa.

[73] Assignee: Adolor Corporation, Malvern, Pa.

[*] Notice: The term of this patent shall not extend beyond the expiration date of Pat. No. 5,667,773.

[21] Appl. No.: 818,559

[22] Filed: Mar. 14, 1997

[51] Int. Cl.⁶ .............................. A61L 9/04; A61K 31/74
[52] U.S. Cl. ............................ 424/45; 424/78.05; 424/47
[58] Field of Search .................................. 424/45, 78.05, 424/47

[56] References Cited

U.S. PATENT DOCUMENTS

| 3,714,159 | 1/1973 | Jannsen et al. | 260/247.2 |
| 3,730,960 | 5/1973 | Watchung et al. | 252/106 |
| 3,884,916 | 5/1975 | Jannsen et al. | 260/247.7 |
| 5,035,883 | 7/1991 | Witkin | 424/78 |
| 5,516,808 | 5/1996 | Sawaya | 514/781 |
| 5,667,773 | 9/1997 | Farrar et al. | 424/78.05 |

*Primary Examiner*—Thurman K. Page
*Assistant Examiner*—Kathryne E. Shelborne
*Attorney, Agent, or Firm*—Imre Balogh

[57] ABSTRACT

Spray formulations of anti-hyperalgesic opiates having a peripheral selectivity of 251 to 1,280 in a solvent mixture of up to 15% w/w alcohol selected from the group consisting of ethyl propyl and isopropyl alcohol and water greater than or equal to 85% w/w water.

16 Claims, No Drawings

SPRAY FORMULATIONS OF ANTIHYPERALGESIC OPIATES AND METHOD OF TREATING TOPICAL HYPERALGESIC CONDITIONS THEREWITH

BACKGROUND OF THE INVENTION

1. Field of the Invention

This invention relates to spray formulations of anti-hyperalgesic opiates having substantially no effects on the central nervous system and method of topically treating hyperalgesic conditions. More particularly, the invention relates to anti-hyperalgesic opiates in non-sting spray formulations for the treatment of topical hyperalgesic conditions associated with injuries.

2. Reported Developments

Pain is the effect of noxious stimuli on nerve endings of a subject which results in the transmission of impulses to the cerebrum. This sensation informs the subject of actual or impending tissue damage and elicits a defensive response. The degree of response substantially correlates with the degree of noxious stimuli in order to speedily avoid further tissue damage and to reestablish normal pre-injury conditions in the subject. The sensation of pain, however, does not end with the stoppage of the noxious stimuli but continues to persist during the inflammation stage of the injury. In turn, the continuation of pain perception causes discomfort to, and deleterously affects the well-being of, the subject. It is, therefore, important to reduce and/or eliminate pain perception of a subject subsequent to injuries.

The reduction/elimination of pain perception can be affected by the central nervous system (hereinafter sometimes referred to as CNS)-mediated analgesia which leads to an overall inhibition of the pain transmission. CNS-mediated analgesia can be effected by systemically administered opiates which, by interaction with specific receptors in the brain and spinal cord, are able to block pain transmission. Systemic opiates, such as morphine, which have been used for many years to control post injury pain, have side effects because their actions within the brain include sedation, depression of respiration, constipation, nausea and development of addiction and dependence. When peripherally applied, opiates have a short duration of action and still possess the undesirable side effects.

Certain opiates, such as loperamide [i.e., 4-(p-chlorophenyl)-4-hydroxy-N-N-dimethyl-αα-diphenyl-1-piperidinebutyramide hydrochloride] and its analogs were reported to be devoid of CNS effects, which is believed to be due to the failure of the opiates to cross the blood brain barrier. Loperamide HCl has been used for a long time in antidiarrheal formulations and has been completely free of the undesirable CNS effects. It is desirable to use such opiates to inhibit/eliminate post-injury pain without concomitant CNS effects.

Spray formulations for topical application for cleansing the injured site are known and have been used by the prior art. Some of these formulations, known as first aid sprays and antiseptics are applied to the site of the injury subsequent to flushing the site with water to remove foreign matter originating from the source of injury or the environment. The substance contained in these sprays kill or prevent the growth of microorganisms. A number of antiseptic drugs are oxidizing agents which include: peroxides, such as hydrogen peroxide; permangenates, such as potassium permangenates, benzene derivatives and phenols. Specific examples of antiseptic agents include chlorhexidine, calcium iodate, iodine, chloroxylenol, hexachlorophene, boric acid and cupric sulfate.

Other pharmaceutical agents used to prevent or combat topical infection and to accelerate the healing process include:

Antibacterial agents, such as Streptomycin, Rifamycin, Ampicillin, Penicillin O, Penicillin V, Bacitracin, Doxycycline, Methacycline, Minocycline, Tetracycline, Acetyl Sulfisoxazole, Succinylsulfathiazole, Sulfaloxic Acid, Sulfapyrazine, and Acetosulfone;

Antifungal agents, such as Dermostatin, Fungichromin, Clotrimazole, Econazole, Potassium Iodide, Propionic Acid, Ketoconazole, Cicloprox Olamine, Tolnaftate and Naftifine;

Anti-inflammatory agents, such as Diclofenac, Tolmetin, Ibuprofen, Protizinic Acid, Glycol Salicylate and Sulfasalazine.

Antibiotics, such as Clindamycin, Erythromycin, Tetracycline, Mupirocin, Bacitracin and Neomycin;

Antiseptic agents such as Chlorhexidine, Calcium Iodate, Iodine, Chloroxylenol, Hexachlorophene, Boric Acid, and Cupric Sulfate; and Antiviral agents, such as Acyclovir, Trifluridine and Zidovudine.

These and other agents used on the site of injury tend to produce stinging, pricking, burning and pain so that their utility to prevent or combat infection and to promote healing is limited to those individuals who are willing to accept these undesirable sensations. This drawback of first aid products is accentuated in the treatment of children having wounds, abrasions and burns who are reluctant to suffer the stinging effect of the products.

Peripheral antihyperalgesic compounds which inhibit sensation of pain without CNS side effects would provide a solution to the problem It has now been discovered that such peripheral antihyperalgesic compounds can render the spray formulations acceptable for delivering agents customarily used in the treatment of topical would abrasions, burns and the like to prevent infection and accelerate wound healing.

In the course of our investigation, however, we have encountered another problem in delivering the spray formulation to the site of treatment. The peripheral antihyperalgesic compounds are essentially insoluble/sparingly soluble in water. Their solubility in water is about 0.002% w/w to 5% w/w. To provide for the inhibition of pain, very large amounts of the peripheral antihyperalgesic compounds were required. The use of such large amounts, on the other hand, resulted clogging of the spray nozzle and deposition of the compounds on the wall of the container from which the aqueous solution of the compounds were dispensed.

While the peripheral antihyperalgesic compounds are soluble in organic solvents, the use of such solvents are very limited for treating topical injuries. The organic solvents having oily consistency tend to hold the active compounds and do not allow quick and sufficient release to the site of injury to be treated.

Other organic solvents without oily consistency, such as methanol, having deleterious affects on open wounds through which they can enter the blood circulation system.

Accordingly, ethanol, propanol and isopropanol were selected as carriers in which the active compounds are soluble and which can be used on open wounds without deleterious side effects. However, these vehicles alone or in an aqueous mixture in which they constituted a substantial amount resulted in stinging and burning sensations rendering the vehicle unsuitable for the delivery of the active agent. Although, during the period of spraying a pleasant cooling effect was observed, the subsequent absorption of the vehicle increased the pain already present at the site of injury.

With extensive experimentation we have now discovered that an effective antihyperalgesic non-sting spray formulation can be provided by incorporating an antihyperalgesic opiate having a peripheral selectivity of from about 251 to about 1,280 in an aqueous alcohol mixture of up to about 15% w/w ethyl-alcohol, propyl alcohol or isopropyl alcohol.

SUMMARY OF THE INVENTION

A topical spray formulation comprising:

(A) a peripheral antihyperalgesic compound of the formula (1)

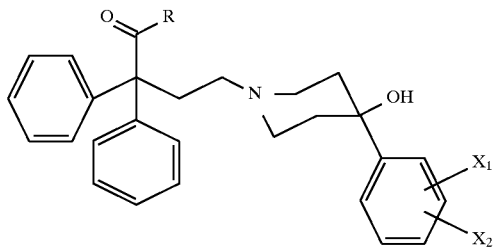

wherein

R is $N(CH_3)_2$, $N(CH_2CH_3)_2$, $N(CH_3)C_2H_5$, $N(CH_2)_4$, $N(CH_2)_5$ or $N(CH_2CH_2)_2O$;

and $X_1$ and $X_2$ are independently H, Cl, Br, F or $CF_3$ and wherein said antihyperalgesic compound has a peripheral selectivity of from about 251 to about 1,280;

(B) a solvent mixture for the compound of formula I comprising: a) up to about 15% w/w of an alcohol selected from the group consisting of ethyl alcohol propyl alcohol and isopropyl alcohol or mixtures thereof; and b) greater than or equal to 85% w/w water, and C) one or more additional active ingredients selected from the group consisting of antibacterials, antivirals, antifungals, anti-inflammatories and anesthetics or mixtures thereof.

The spray formulations may be contained in a propellant mixture or they may be dispensed from a pump-action container or the like.

Preferred antihyperalgesic compounds used in the present invention are:

(1) 1-[4(4Hydroxy-4phenyl-1-piperidino)-2,2-diphenylbutyryl]piperidine
[R=$N(CH_2)_5$; $X_1$=H; $X_2$=H]

(2) 4-(p-Chlorophenyl)-4-hydroxy-N-ethyl-N-methyl-ααdiphenyl-1-piperidinebutyramide
[R=NMe Et; $X_1$=4-Cl; $X_2$=H]

(3) 4-(p-Bromophenyl)-4-hydroxy-N,N-dimethyl-αα-diphenyl-1-piperidinebutyramide
[R=$NMe_2$; $X_1$=4-Br; $X_2$=H]

(4) 1-{4-[(3,4-Dichlorophenyl)-4-hydroxy-1-piperidino-2,2diphenylbutyryl}pyrrolidine
[R=$N(CH_2)_4$; $X_1$=4-Cl]

(5) 1-{4-[(4-Chlorophenyl)4-hydroxy- 1-piperidino]-2,2-diphenylbutyryl}pyrrolidine
[R=$N(CH_2)_4$; $X_1$=4-Cl; $X_2$=H]

(6) 4-(p-Chlorophenyl)-4-hydroxy-N,N-dimethyl-αα-diphenyl-1-piperidinebutyramide
[R=$NMe_2$; $X_1$ (7) 4-(p-Fluorophenyl)-4-hydroxy-N,N-dimethyl-αα-diphenyl-1-piperidinebutyramide
[R=NMe2; $X_1$=4-F; $X_2$=H]

(8) 4-(4-Chloro₃-trifluoromethyl-phenyl)-4-hydroxy-N,N-dimethyl-αα-diphenyl-1-piperidinebutyramide
[R=$NMe_2$; $X_1$=3-$CF_3$]

(9) 1-[4-(4-Hydroxy-4phenyl-1piperidino)-2,2-diphenylbutyryl]pyrrolidine and
[R=$N(CH_2)_4$; $X_1$=H; $X_2$=H]

(10) 1-{Hydroxy4-(3-tifluoromethylphenyl)-1-piperidino]-2,2-diphenylbutyryl} morpholine
[R=$N(CH_2CH_2)_2O$; $X_1$=3-$CF_3$; $X_2$=4-H]

The peripheral selectivity of these compounds are shown in Table I.

TABLE I

| Compound | Peripheral Selectivity ($ED_{50tw}/ED_{50}$ Castor Oil) |
|---|---|
| 1 | >1,280 |
| 2 | ≧1,231 |
| 3 | 800 |
| 4 | >640 |
| 5 | 593 |
| 6 | 533 |
| 7 | 500 |
| 8 | 467 |
| 9 | 437 |
| 10 | >251 |

Peripheral selectivity is defined by the ratio of the $ED_{50}$ in the tail-withdrawal assay over the $ED_{50}$ in the anti-diarrheal assay. The assay results for the above listed compounds were obtained by the test methods described hereunder.

Measure of Centrally-Mediated Opiod Analgesia by the Tail-Withdrawal Assay (Janssen, P. A. J.; Niemegeers, C. J. E.; Dony, J. G. H., The Inhibitory effect of Fentanyl and other morphine-like analgesics on the warm water induced tail withdrawal reflex in rats. Arzneimittel-Forschung 1963, 13, 502–507.)

Young female Wistar rats (170–210 g body weight) are used only once. They are fed and watered ad libitum in their living quarters until 7:00 AM of the day of the experiment, when they are brought to the laboratory to be put into individual restraining cages on hour later until the end of the experiment. The lower 5 cm portion of the tail is marked. Around 8:30 AM the "normal" reaction time of each rat is determined by immersing the lower 5 cm portion of the tail in a cup freshly filled with water from a large constant temperature (55° C.) bath until the typical tail withdrawal response is observed. The cut off time is 15 seconds. The reaction time is measured in 0.5 second units with a stopwatch. After each determination the tail is carefully dried. Around 9:00 AM each rat is given saline (control rats) or an aqueous solution (or suspension) of the substance to be investigated by the oral route of administration. Periodically thereafter (i.e., ¼, ½, 1, 2, 3, 4, 5 and 6 hours after dosage) the reaction time is again measured by trained technicians unaware of the nature of the compounds. Results of these studies are expressed as $ED_{50}$ concentration values (mg/kg), calculated as the dose producing a tail withdrawal latency equal to half the difference between the maximum latency (≦15 seconds) and the baseline latency (6 to 8 seconds).

Castor Oil Test in Rats

[see, e.g. Niemegeers et al (1972) Arzneim Forsch, 22:516–518; U.S. Pat. No. 4,867,979; U.S. Pat. No. 4,990,521; U.S. Pat. No. 4,824,853]

Young female Wistar rats (230–250 g body weight) are fasted overnight and in the morning each animal is treated orally with a dose level of the compound to be tested. One hour thereafter, the animal received 1 ml of castor oil orally. Each animal is kept in an individual cage. At different selected time intervals (e.g. 1,2,3,4,6 and 8 hrs) after the castor oil treatment, the presence or absence of diarrhea is noted. In more than 95% of 500 control animals, severe diarrhea is observed 1 hour after treatment with castor oil. Using this all-or-none criterion, a significant positive effect occurs with the tested compound if no diarrhea is observed 1 hour after the castor oil treatment. A minimum of 5 dose levels are use per drug, each dose level being given to 10 rats on ten different days. The $ED_{50}$ value is determined as that dose in mg/kg body weight at which no diarrhea is present in 50% of the tested animals.

The solvent mixture for the compound of formula I is preferably of from about 1% w/w to 15% w/w, more preferably of from 2 to 10% w/w, and most preferably of from 5 to 8% w/w of an alcohol selected from the group consisting of ethanol, propanol or isopropanol and of from about 99% w/w to about 85% w/w water.

DETAILED DESCRIPTION OF THE INVENTION

The Anti-Hyperalgesic Compounds

The compounds for use in the compositions and methods herein possess peripheral anti-hyperalgesic and substantially no CNS activities because they do not cross the blood brain barrier. The failure to cross the blood brain barrier precludes the occurrence of the CNS systemic side effects, so that there is no potential for abuse. The compounds for use in the methods and compositions provided herein include compounds that by virtue of its interaction, either directly or indirectly, with peripheral opioid receptors ameliorates the peripheral hyperalgesic state, but does not exhibit systemic CNS-mediated analgesic activity or CNS side effects, including heaviness of the limbs, flush or pale complexion, clogged nasal and sinus passages, dizziness, depression, respiratory depression, sedation and constipation. These compounds include antidiarrheals that act as antidiarrheals via interaction, with μ, δ, κ receptors, and opiate agonists, such as metkephamide and related enkephalin analogs. The compounds of the present invention have been reported in prior art patents U.S. Pat. Nos. 3,714,159 and 3,884,916 which are incorporated herein by reference.

Representative examples are included according to said patents to illustrate the preparation of some compounds used in the present invention.

EXAMPLE 1

1-[4-(4-Hydroxy4-phenylpiperidino)-2,2-diphenylbutyryl]piperidine hydrochloride

A mixture of 13.5 parts of 1-(tetrahydro-3,3-diphenyl-2-furylidene) piperidinium bromide, 5.3 parts of 4-phenyl-4-piperidinol, 8 parts of sodium carbonate, 0.2 parts of potassium iodide and 200 parts of 4-methyl-2-pentanone is stirred and refluxed for 3 hours with water-separator. The reaction mixture is cooled and 200 parts of water is added. The organic layer is separted, dried and evaporated. The solid residue is crystallized from 120 parts of 4-methyl-2-pentanone (activated charcoal), yielding 7.8 parts of the crude free base of 1-[4-(4-hydroxy-4-phenyl-piperidino)-2,2diphenylbutyryl]piperidine hydrochloride. It is dissolved in 4-methyl-2-pentanone and this solution is acidified with an excess of 2-propanol previously saturated with gaseous hydrogen chloride. The precipitated salt is filtered off and dried, yielding 1-[4-(4-hydroxy-4-phenylpiperidino)-2,2-diphenylbutyryl]piperidine hydrochloride; m.p. 240.3° C.

EXAMPLE 2

4-(p-Chlorophenyl)4-hydroxy-N,N-dimethyl-α, α-diphenylpiperidine-1-butyramide hydrochloride A mixture of 6.33 parts of 4-(p-chlorophenyl)-4piperidinol, 8 parts sodium carbonate, 0.2 parts of potassium iodide and 240 parts of 4-methyl-2-pentanone is distilled azeotropically. Then there are added 12.12 parts of dimethyl (tetrahydro-3,3-diphenyl-2-furylidene)ammonium bromide and the whole is stirred and refluxed for about 15 hours. The reaction mixture filtered hot and the filtrate is evaporated. The oily residue is dissolved in 2-propanol and to this solution is added an excess of 2-propanol previously saturated with gaseous hydrogen chloride. The whole is evaporated and the oily residue is warmed in diluted hydrochloric acid solution. Upon the addition of toluene, the salt is precipitated. It is filtered off, boiled in acetone, and filtered off again after cooling, yielding 4-(p-Chlorophenyl)-4-hydroxy-N,N-dimethyl-α,α-diphenyl-piperidine-1-butyramide hydrochloride; m.p. 221.1° C.

EXAMPLE 3

1-[4-(4-Hydroxy4-phenylpiperidino)-2,2-diphenylbutyryl]pyrrolidine

A mixture of 13 parts of 1-(tetrahydro-3,3-diphenyl-2-furylidene) pyrrolidinium bromide, 5.3 parts of 4-phenyl-4-piperidinol 8 parts of sodium carbonate, 0.2 parts of potassium iodide and 200 parts of 4-methyl-2-pentanone is stirred and refluxed for 5 hours with water separator. The reaction mixture is cooled and water is added. The organic layer s separated, washed with diluted sodium hydroxide solution, dried, filtered, and while stirring the filtrate, the product is crystallized. It is filtered off and dried, yielding 1-[4-(4-hydroxy-4-phenylpiperidino)-2,2-diphenylbutyryl]pyrrolidine; m.p. 187.5° C.

EXAMPLE 4

4-(4-Chloro-3-trifluoromethylphenyl)-4-hydroxy-N,N-dimethyl-α,α-diphenylpiperidine-1- butyramide hydrochloride A mixture of 12.1 parts of dimethyl (tetrahydro-3,3-diphenyl-2-furylidene) ammonium bromide, 8.4 parts of 4-(4-chloro-3-trifluoromethylphenyl)-4-piperidinol, 8 parts of sodium carbonate, 0.4 parts of potassium iodide and 200 parts of 4-methyl-2-pentanone is stirred and refluxed for 3 hours with water separator. The reaction mixture is cooled and water is added. The organic layer is separated, washed with diluted sodium hydroxide solution, dried and concentrated to a volume of about 200 parts. The concentrate is acidified with an excess of 2-propanol previously saturated with gaseous hydrogen chloride. Upon stirring, the salt is crystallized. It is filtered off and dried, yielding 4-(4-chloro-3-trifluoromethylphenyl)-4-hydroxy-N,N-dimethyl-α,α-diphenylpiperidine-1-butyramide hydrochloride; m.p. 215.3° C.

EXAMPLE 5

4-(p-Bromophenyl)-4-hydroxy-N,N-dimethyl-α,α-diphenylpiperidine-1butyramide hydrate A mixture of 12.1 parts of dimethyl (tetrahydro-3,3-diphenyl-2-furylidene) ammonium 10 bromide, 8.8 parts of 4-(p-bromophenyl)-4-piperidinol hydrochloride, 10.6 parts of sodium carbonate, 0.5 parts of potassium iodide and 200 parts of 4-methyl-2-pentanone is stirred and refluxed for 14 hours with water separator. The reaction mixture is cooled and water (200 parts) is added. The organic layer is separated, washed with diluted sodium hydroxide solution, dried, filtered, and while stirring the filtrate, the product is crystallized. It is filtered off and recrystallized from 80 parts of 4-methyl-2-pentanone (activated charcoal), yielding 4-(p-bromophenyl)-4-hydroxy-N,N-dimethyl-α,α-diphenylpiperidine-1-butyramide hydrate; m.p. 123.7° C.

The anti-hyperalgesic compounds are dissolved in the alcohol-water mixture and can be dispensed as anti-hyperalgesic spray from containers having a pump action or from aerosol containers which are charged with propellants. The spray on the site of injury will inhibit pain without causing a stinging or burning sensation to the patient. However, it is preferable to include other pharmaceutical agents such as antibacterial, antivirals, antifungals, anti-inflammatories and antiseptics which will prevent or eliminate infection and help the healing process.

Antibacterial Agents/Antibiotics

Suitable antibacterial agents include: Aminoglycosides, Amphenicols, Ansamycins, β-Lactams, Carbapenems, Cephalosporins, Cephamycins, Monobactams, Oxacephems, Penicillins, Lincosamides, Macrolides, Amphomycin, Bacitracin, Capreomycin, Colistin, Enduracidin, Enviomycin, Fusafungine, Gramicidin(s), Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin Zinc Bacitracin, Tetracyclines, Cycloserine, Mupirocin, Tuberin, 2,4-Diaminopyrimidines, Nitrofurans, Quinolones, Sulfonamides, Sulfones, Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine, and Zibornol.

Preferred antibacterial agents/antibiotics include: Clindamycin, Erythromycin, Tetracycline, Mupirocin, Bacitracin and Neomycin.

Antifungal Agents

Suitable antifungal agents include: Polyenes, Allylamines, Imidazoles, Triazoles, Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salidylanilide, Sulbentine, Tenonitrozole, Tolciclate, Tolindate, Tolnaftate, Tricetin, Ujothion, and Undecylenic Acid.

Preferred antifungal agents include: Ketoconazole, Clotrimazole, Ciclopirox olamine, Tolnaftate and Naftifine.

Anti-inflammatory Agents

Suitable Anti-inflammatory agents include: Corticosteroids, Aminoarylcarboxylic Acid Derivatives, Arylacetic Acid Derivatives, Arylbutyric Acid Derivatives, Arylcarboxylic Acids, Arylpropionic Acid Derivatives, Pyrazoles, Pyrazolones, Salicylic Acid and derivatives thereof, Thiainecarboxamides, E-Acetamidocaproic Acid, S-Adenosylmethionine, 3-Amino-4-hydroxy-butyric Acid, Amixetrine, Bendazac, Bucolome, Carbazones, Difenpiramide, Ditazol, Guaiazulene, Heterocyclid Aminoalkyl Esters of Mycophenolic Acid and derivatives thereof, Nabumetone, Nimesulide, Orgotein, Oxaceprol, Oxazole derivatives, Paranyline, Pifoxime, 2-substituted-4,6di-tertiary-butyl-s-hydroxy-1,3-pyrimidines, Proquazone and Tenidap.

Antiseptics

Suitable antiseptics include: Guanidines, Halogens/Halogen Compounds, Nitrrofurans, Phenols, Quinolines, Boric Acid, Chloroazodin, m-Cresyl Acetate, Cupric Sulfate and Ichthammol.

Antiviral Agents

Suitable antiviral agents include: Purines/Pyrimidinones, Acetylleucine, Monoethanolamine, Acridinanide, Alkylisooxazoles, Amantadine, Amidinomycin, Cuminaldehyde Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

Dispensing the Compositions

The compositions of the present invention may be dispensed as a liquid form a conventional spray bottle by pumping action by which the bottle is air-pressurized and the liquid is expelled in a relatively fine spray form.

The preferred way of dispensing the compositions of the present invention is in the form of aerosols. Compositions for administration as aerosols are prepared by dissolving an anti-hyperalgesic compound of formula I in the aqueous solution of up to 15% w/w ethanol propanol or isopropanol mixing with a volatile propellant, and placing the mixture in a pressurized container having a metering valve to release the mixture in extra fine droplet size.

The liquefied propellant employed typically is one which has a boiling point below ambient temperature at atmospheric pressure. For use in compositions intended to produce aerosols for medicinal use, the liquefied propellant should be non-toxic. Among the suitable liquefied propellants which can be employed are the lower alkanes containing up to five carbon atoms, such as butane and pentane, or an alkyl chloride, such as methyl, ethyl or propyl chlorides. Further suitable liquefied propellants are the fluorinated and fluorochlorinated alkanes such as are sold under the trademarks "Freon" and "Genetron". Mixtures of the above mentioned propellants can suitably be employed.

Preferred liquefied propellants are chlorine free propellants, for example 134a (tetrafluoroethane) and 227c (heptafluoropropane) which can be used as described above. The aerosol sprays are made by nebulizing the solution containing the anti-hyperalgesic compound, using a variety of known nebulizing techniques. The aerosol system consists of a solution of the anti-hyperalgesic compound, and other therapeutic agents, if desired, in a liquid propellant. Both liquid and vapor phases are present in a pressurized container and when a valve on the container is opened, liquid propellant containing the dissolved anti-hyperalgesic compound, and other therapeutic agents, is released in the form of a fine aerosol m 2. The topical anti-hyperalgesic spray formulation of claim 1 wherein said anti-hyperalgesic compound is selected from the group consisting of:

1-[4-(4-Hydroxy-4-phenyl-1-piperidino-2, 2diphenylbutyryl]piperidine 4-(p-Chlorophenyl)-4-hydroxy-N-ethyl-N-methyl-α,α-diphenyl-1-piperidinebutyramide 4-(p-Bromophenyl)-4-hydroxy-N,N-dimethyl-α,α-diphenyl-1-piperidinebutyramide 1-{(4-[(3,4-Dichlorophenyl)-4-hydroxy-1-piperidino]-2, 2-diphenylbutyryl}pyrrolidine 1-{(4-[(4-Chlorophenyl)-4-hydroxy-1-piperidino]-2,2-diphenylbutyryl}pyrrolidine 4-(p-Chlorophenyl)-4-hydroxy-N,N-dimethyl-α,α-diphenyl-1-piperidinebutyramide 4-(p-Fluorophenyl)4-hydroxy-N,N-dimethyl-α,α-diphenyl-1-piperidinebutyramide 4-(4Chloro-3-trifluoromethyl-phenyl)-4-hydroxy-N,N-dimethyl-α,α-diphenyl-1-piperidinebutyramide 1-[4(4-Hydroxy-4-phenyl-1-piperidino)-2,2-diphenylbutyryl]pyrrolidine and 1-{4-[4-Hydroxy4-(3-trifluoromethylphenyl)-1-piperidino-2,2-diphenylbutyryl} morpholine.

3. The topical anti-hyperalgesic spray formulation of claim 1 further comprising one or more additional active ingredients selected from the group consisting of antibacterials, antivirals, antifungals, anti-inflammatories, anesthetics and mixtures thereof.

4. The topical anti-hyperalgesic spray formulation of claim 3 wherein said antibacterial is selected from the group consisting of:

Aminoglycosides, Amphenicols, Ansamycins, β-Lactams, Carbapenems, Cephalosporins, Cephamycins, Monobactams, Oxacephems, Penicillins, Lincosamides, Macrolides, Amphomycin, Bacitracin, Capreomycin, Colistin, Enduracidin, Enviomycin, Fusafungine, Gramicidin(s), Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin Zinc Bacitracin, Tetracyclines, Cycloserine, Mupirocin, Tuberin, 2,4-Diamninopyrimidines, Nitrofurans, Quinolones, Sulfonamides, Sulfones, Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine, Zibornol Clindamycin, Erythromycin, Tetracycline, Mupirocin, Bacitracin and Neomycin.

5. The topical anti-hyperalgesic spray formulation of claim 3 wherein said antiseptic is selected from the group consisting of:

Guanidines, Halogens/Halogen Compounds, Nitrrofurans, Phenols, Quinolines, Boric Acid, Chloroazodin, m-Cresyl Acetate, Cupric Sulfate and Ichthammol.

6. The topical anti-hyperalgesic spray formulation of claim 3 wherein said antiviral agent is selected from the group consisting of:

Purines/Pyrimidinones, Acetylleucine, Monoethanolamine, Acridinamide, Alkylisooxazoles, Amantadine, Amidinomycin, Cuminaldehyde, Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

7. The topical anti-hyperalgesic spray formulation of claim 3 wherein said antifungal agent is selected from the group consisting of:

Polyenes, Allylamines, Imidazoles, Triazoles, Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salidylanilide, Sulbentine, Tenonitrozole, Tolciclate, Tolindate, Tolnaftate, Tricetin, Ujothion, Undecylenic Acid, Ketoconazole, Clotrimazole, Ciclopirox olamine, Tolnaftate and Naftifine.

8. The topical anti-hyperalgesic spray formulation of claim 3 wherein said anti-inflammatory agent is selected from the group consisting of:

Corticosteroids, Aminoarylcarboxylic Acid Derivatives, Arylacetic Acid Derivatives, Arylbutyric Acid Derivatives, Arylcarboxylic Acids, Arylpropionic Acid Derivatives, Pyrazoles, Pyrazolones, Salicylic Acid and derivatives thereof, Thiazinecarboxamides, E-Acetamidocaproic Acid, S-Adenosylmethionine, 3-Amino-4-hydroxy-butyric Acid, Amixetrine, Bendazac, Bucolome, Carbazones, Difenpiramide, Ditazol, Guaiazulene, Heterocyclid Aminoalkyl Esters of Mycophenolic Acid and derivatives thereof, Nabumetone, Nimesulide, Orgotein, Oxaceprol, Oxazole derivatives, Paranyline, Pifoxime, 2-substituted-4,6di-tertiary-butyl-s-hydroxy-1,3-pyrimidines, Proquazone and Tenidap.

9. A method of inhibiting hyperalgesic activity comprising topically applying an effective amount of an anti-hyperalgesic spray formulation to a mammal in need of such treatment, said anti-hyperalgesic spray formulation comprising:

(A) a peripheral anti-hyperalgesic compound of the formula (I)

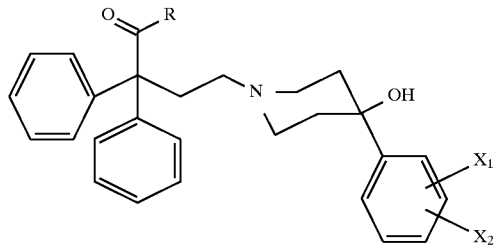

R is $N(CH_3)_2 N(CH_2CH_3)_2 N(CH_3)C_2H_5$, $N(CH_2)_4$, $N(CH_2)_5$ or $N(CH_2CH_2)_2O$;

and $X_1$ and $X_2$ are independently H, Cl, Br, F or $CF_3$ and wherein said antihyperalgesic compound has a peripheral selectivity of from about 251 to about 1,280;

(B) a solvent mixture for the compound of formula I comprising: a) up to about 15% w/w of an alcohol selected from the group consisting of ethyl alcohol, propyl alcohol and isopropyl alcohol or mixtures thereof; and b) greater than or equal to 85% w/w water.

10. The method of claim 9 wherein said anti-hyperalgesic compound is selected from the group consisting of:

1-[4-(4-Hydroxy-4-phenyl-1-piperidino-2,2diphenylbutyryl]piperidine 4-(p-Chlorophenyl)-4-hydroxy-N-ethyl-N-methyl-α,α-diphenyl-1-piperidinebutyramide 4-(p-Bromophenyl)-4-hydroxy-N,N-dimethyl-α,α-diphenyl-1-piperidinebutyramide 1-{(4-[(3,4-Dichlorophenyl)-4-hydroxy-1-piperidino]-2,2-diphenylbutyryl}pyrrolidine 1-{(4-[(4-Chlorophenyl)-4-hydroxy-1-piperidino]-2,2-diphenylbutyryl}pyrrolidine 4-(p-Chlorophenyl)-4-hydroxy-N,N-dimethyl-α,α-diphenyl-1-piperidinebutyramide 4-(p-Fluorophenyl)4-hydroxy-N,N-dimethyl-α,α-diphenyl-1-piperidinebutyramide 4-(4Chloro-3-trifluoromethyl-phenyl)-4-hydroxy-N,N-dimethyl-α,α-diphenyl-1-piperidinebutyramide 1-[4(4-Hydroxy-4-phenyl-1-piperidino)-2,2-diphenylbutyryl]pyrrolidine and 1-{4-[4-Hydroxy4-(3-trifluoromethylphenyl)-1-piperidino-2,2-diphenylbutyryl} morpholine.

11. The method of claim 9 wherein said anti-hyperalgesic composition further comprises one or more additional active ingredients selected from the group consisting of antibacterials, antivirals, antifungals, anti-inflammatories, anesthetics and mixtures thereof.

12. The method of claim 11 wherein wherein said antibacterial is selected from the group consisting of:

Aminoglycosides, Amphenicols, Ansamycins, β-Lactams, Carbapenems, Cephalosporins, Cephamycins, Monobactams, Oxacephems, Penicillins, Lincosamides, Macrolides, Amphomycin, Bacitracin, Capreomycin, Colistin, Enduracidin, Enviomycin, Fusafungine, Gramicidin(s), Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin Zinc Bacitracin, Tetracyclines, Cycloserine, Mupirocin, Tuberin, 2,4-Diaminopyrimidines, Nitrofurans, Quinolones, Sulfonamides, Sulfones, Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine, Zibornol, Clindamycin, Erythromycin, Tetracycline, Mupirocin, Bacitracin and Neomycin.

13. The method of claim 11 wherein said antiseptic is selected from the group consisting of:

Guanidines, Halogens/Halogen Compounds, Nitrrofurans, Phenols, Quinolines, Boric Acid, Chloroazodin, m-Cresyl Acetate, Cupric Sulfate and Ichthammol.

14. The method of claim 11 wherein said antiviral agent is selected from the group consisting of:

Purines/Pyrimidinones, Acetylleucine, Monoethanolamine, Acridinamide, Alkylisooxazoles, Amantadine, Amidinomycin, Cuminaldehyde, Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

15. The method of claim 11 wherein said antifungal agent is selected from the group consisting of:

Polyenes, Allylamines, Imidazoles, Triazoles, Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salidylanilide, Sulbentine, Tenonitrozole, Tolciclate, Tolindate, Tolnaftate, Tricetin, Ujothion, Undecylenic Acid, Ketoconazole, Clotrimazole, Ciclopirox olamine, Tolnaftate and Naftifine.

16. The method of claim 11 wherein said anti-inflammatory agent is selected from the group consisting of:

Corticosteroids, Aminoarylcarboxylic Acid Derivatives, Arylacetic Acid Derivatives, Arylbutyric Acid Derivatives, Arylcarboxylic Acids, Arylpropionic Acid Derivatives, Pyrazoles, Pyrazolones, Salicylic Acid and derivatives thereof, Thiazinecarboxamides, E-Acetamidocaproic Acid, S-Adenosylmethionine, 3-Amino-4-hydroxy-butyric Acid, Amixetrine, Bendazac, Bucolome, Carbazones, Difenpiramide, Ditazol, Guaiazulene, Heterocyclid Aminoalkyl Esters of Mycophenolic Acid and derivatives thereof, Nabumetone, Nimesulide, Orgotein, Oxaceprol, Oxazole derivatives, Paranyline, Pifoxime, 2-substituted-4,6-di-tertiary-butyl-s-hydroxy-1,3-pyrimidines, Proquazone and Tenidap.

* * * * *